United States Patent

Sheridan et al.

[11] Patent Number: 5,829,980
[45] Date of Patent: Nov. 3, 1998

[54] GASKET FOR VACUUM THERMOFORMING MACHINE

[76] Inventors: John J. Sheridan, 821 Old Metairie Dr., Metairie, La. 70001; Dann A. Schwartz, 3936 Peoples St., Metairie, La. 70002

[21] Appl. No.: 627,147

[22] Filed: Mar. 4, 1996

[51] Int. Cl.$^6$ .............................. A61C 13/08; B29C 51/10
[52] U.S. Cl. ........................ 433/213; 425/388; 264/554; 428/131
[58] Field of Search .............................. 433/213; 425/388, 425/DIG. 60, DIG. 47; 264/222, 554; 277/11, 235 B, 237 R; D23/269; 428/66.4, 131

[56] References Cited

U.S. PATENT DOCUMENTS

| D. 269,111 | 5/1983 | Logsdon | D23/269 |
|---|---|---|---|
| 2,139,631 | 12/1938 | Dresch et al. | 264/554 |
| 3,156,012 | 11/1964 | Hritz | 425/388 |
| 3,307,222 | 3/1967 | Baldwin | 425/388 |
| 3,377,656 | 4/1968 | Tilden | 425/388 |
| 3,416,520 | 12/1968 | Creager, Jr. | 128/850 |
| 3,532,776 | 10/1970 | Kopp | 264/554 |
| 3,682,571 | 8/1972 | Greenberg et al. | 264/554 |
| 4,050,457 | 9/1977 | Davidson | 428/131 |
| 4,798,534 | 1/1989 | Breads | 433/213 |
| 4,944,901 | 7/1990 | Kwok | 425/388 |
| 5,240,759 | 8/1993 | Layton | 428/131 |

FOREIGN PATENT DOCUMENTS

| 210513 | 3/1956 | Australia | 4/245.1 |
|---|---|---|---|
| 4427 | 12/1891 | Switzerland | 4/245.1 |

*Primary Examiner*—Ralph A. Lewis
*Attorney, Agent, or Firm*—John M. Harrison

[57] ABSTRACT

A gasket for vacuum thermoforming machines, which gasket is designed to be positioned on the perforated base plate of the thermoforming machine to cover selected ones of the vacuum openings in the base plate. An opening is provided in the center of the gasket for concentrating the vacuum in this area and increasing the vacuum applied to a heated plastic sheet or plate positioned above a dental impression cast located on the base plate in the gasket vacuum opening. The vacuum applied by the vacuum thermoforming machine is thus concentrated within the confines of the vacuum opening of the gasket to more efficiently mold the soft plastic plate over the dental impression cast and form a plastic retainer for straightening teeth. A method for molding a plastic retainer for straightening teeth, which method includes the steps of placing a gasket having a vacuum opening over the perforated base plate of a vacuum thermoforming machine such that some of the vacuum openings are covered by the gasket and others are exposed in the vacuum opening in the gasket; positioning a plastic plate above the gasket adjacent to the heater in the vacuum thermoforming machine; placing a dental impression cast on the perforated base plate in the opening in the gasket; heating the plastic plate; initiating the vacuum in the perforations in the base plate defined by the opening in the gasket; and lowering the softened plastic plate over the dental impression. Additional, and/or oversized perforations may also be provided in the gasket vacuum opening to increase the vacuum applied to the plastic plate.

6 Claims, 2 Drawing Sheets

GASKET FOR VACUUM THERMOFORMING MACHINE

BACKGROUND OF THE INVENTION

Field of the Invention

This invention relates to an apparatus and technique for dentistry and more particularly, to an apparatus and technique for molding a plastic orthodontic correction appliance or retainer.

Retainers have classically been fashioned from wire and plastic or wires and metal brackets that are temporarily bonded to the teeth to apply pressure on the teeth to straighten the teeth. Application of these devices is laborious and expensive and considerable time is required to effect a desired straightening of the teeth. Furthermore, the wire and bracket combination is unsightly, highly visible on the teeth and is therefore objectionable to many patients. Moreover, when the braces are to be removed, pressure must be applied to the metal brackets in order to loosen the adhesive which joins the metal brackets to the teeth, resulting in additional labor, expense and possible damage to the teeth.

In recent years, plastic retainers have become popular with the advent of pressure and vacuum thermoforming machines, in large measure because the plastic retainers are transparent, thereby presenting a much more satisfactory esthetic appearance. The plastic retainers also have the advantage of more efficiently straightening the teeth since adjustments can be made to the retainers with time to expedite straightening of the teeth.

One of the problems which exists in the use of vacuum thermoforming units and equipment is the practical limitations of vacuum formed by these devices. For example, at best, a vacuum thermoforming unit can only generate a little less than about 30 psi. However, it has been found that when this reduced pressure is concentrated in a small area it is possible to increase the efficiency of the available vacuum-forming power and therefore the efficiency of eveloping a dental impression cast with plastic in a degree of fit necessary to effect straightening of the teeth in an optimum manner. It has surprisingly been found that concentrating the vacuum on a thermoforming unit by blocking the peripheral holes on the base plate is easily accomplished by using a gasket that covers the outer peripheral vacuum holes in the base plate. When the vacuum is initiated, the gasket effectively blocks the outer peripheral holes, thus concentrating the vacuum into the center of the unit in an opening in the gasket where the dental impression cast to be plastic overlaid is placed. The inner ring of peripheral holes in the vacuum thermoforming base plate are open to assure plastic adaptation. It has also been found that the vacuum openings in the vacuum unit base plate are usually too few and/or small to effect an optimum vacuum for the purpose of this invention and the holes are preferably increased in number and/or drilled to at least one-eighth of an inch in diameter within the confines of the opening in the gasket. It has been found that these modifications, together with use of a dental impression cast that has been trimmed to minimal dimensions, produces a thermoformed plastic retainer or appliance of very high quality at very little cost and with minimum effort.

Accordingly, it is an object of this invention to provide a new and improved technique for manufacturing a thermoformed plastic dental appliance or retainer of high quality by using a gasket to increase the vacuum in a vacuum thermoforming unit.

Another object of this invention is to provide a method for forming plastic dental appliances and retainers of high quality by concentrating the vacuum on a thermoforming unit using a gasket having a central opening.

Still another object of this invention is to provide a gasket for concentrating the vacuum in a vacuum thermoforming machine, which gasket is characterized by an opening of selected size to accommodate a selected number of standard or oversized vacuum openings in the thermoforming unit base plate, concentrate the vacuum in the area of a dental impression cast and produce an orthodontic retainer and appliance of exceptionally tight fit and quality.

Yet another object of the invention is to provide a new and improved gasket for fitting over the base plate of a vacuum thermoforming machine to block a selected number of the vacuum openings, concentrate the vacuum in an opening in the gasket at the area of the dental impression cast and tightly fit heated plastic retainer material over the dental impression cast to produce a retainer or appliance of exceptionally high quality.

A still further object of this invention is to provide a method for molding a plastic retainer for straightening teeth, which includes the steps of placing a gasket having a vacuum opening over the perforated base plate of a vacuum thermoforming machine such that some of the vacuum openings are covered by the gasket and others are exposed in the vacuum opening in the gasket; positioning a plastic sheet or plate above the gasket adjacent to the heater in the vacuum thermoforming machine; placing a dental impression cast on the perforated base plate in the opening in the gasket; heating the plastic plate; initiating the vacuum in the perforations in the base plate defined by the opening in the gasket; and lowering the heat-softened plastic plate over the dental impression to vacuum-form the heated plastic on the dental impression.

SUMMARY OF THE INVENTION

These and other objects of the invention are provided in a new and improved technique for increasing the vacuum output of a vacuum thermoforming unit using a gasket fitted over the base plate to block selected ones of the vacuum openings and expose other vacuum openings in the area of the dental impression cast placed on the base plate, wherein a heated and softened plastic plate of selected thickness is applied to the dental impression cast with an exceptionally tight fit caused by the increased vacuum. The technique includes optionally drilling the conventional holes in the base plate to a diameter of at least ⅛ of an inch and/or providing additional oversized or standard holes in the area of the base plate exposed by the opening in the gasket.

The invention also includes a gasket for increasing the vacuum in a vacuum thermoforming unit, which gasket is designed to cover selected openings in the perforated vacuum thermoforming unit base plate and expose other openings in the area of a dental impression cast to facilitate molding of a plastic retainer or appliance of exceptionally tight fit and high quality over the dental impression cast.

BRIEF DESCRIPTION OF THE DRAWINGS

The invention will be better understood by reference to the accompanying drawing, wherein.

DESCRIPTION OF THE PREFERRED EMBODIMENTS

Figure 2:
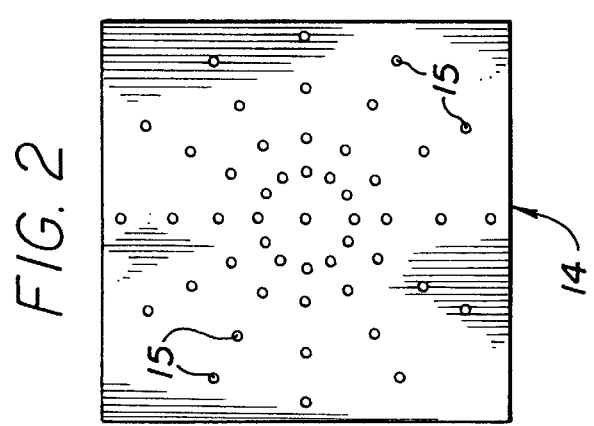
FIG. 2 is a top view of the conventional perforated base plate on the vacuum thermoforming machine illustrated in FIG. 1.
Figure 1:
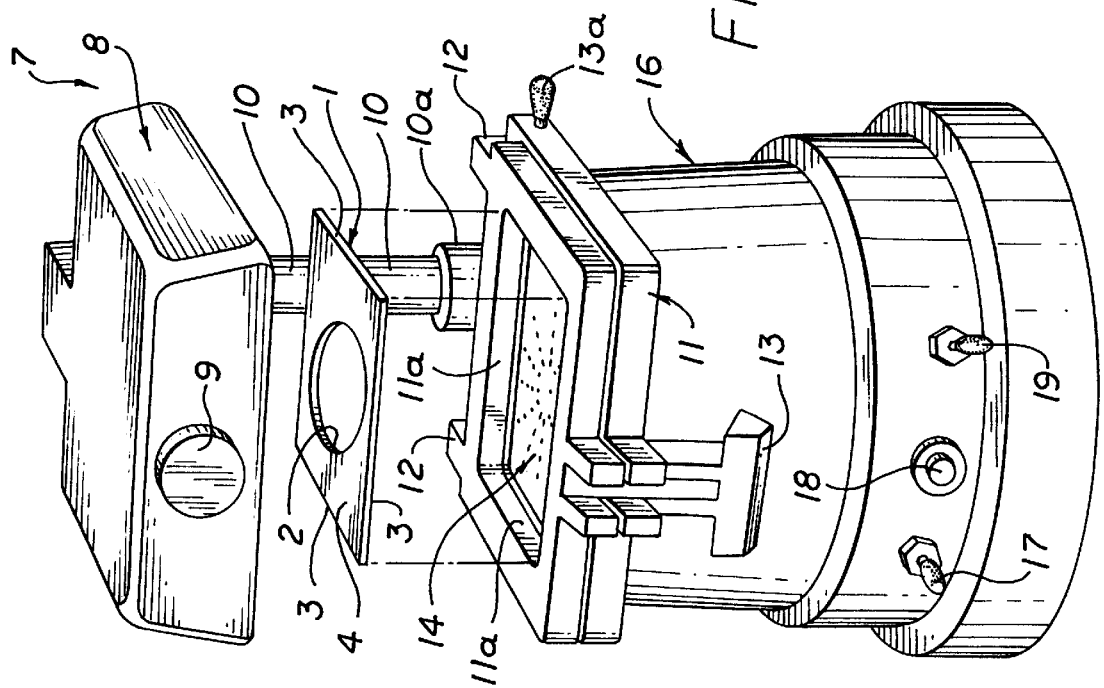
FIG. 1 is a perspective view of a typical vacuum thermoforming unit with the gasket of this invention positioned for location on the perforated base plate thereof.

Referring initially to FIGS. 1 and 2 of the drawing a conventional vacuum thermoforming machine is generally illustrated by reference numeral 7. The vacuum thermoforming machine 7 includes a heating unit 8, positioned above a base 16 and having a heating unit handle 9, as illustrated. A vertical post 10 extends downwardly from attachment to the heating unit 8 and extends through a post seat 10a, to mount in the base 16. Accordingly, the heating unit 8 is fixed with respect to the base 16 and a frame boss 11 is slidably mounted on the post 10 by means of the post seat 10a and is split, with the split portions connected by a frame boss hinges 12. Consequently, the top portion of the frame boss 11 can be hinged upwardly on the frame boss hinges 12 with respect to the bottom portion of the frame boss 11. A pair of frame elevation knobs 13a are provided on the frame boss 11 and the frame boss 11 seats on a perforated base plate 14 provided on the base 16 of the vacuum thermoforming machine 7. The base plate 14 is fitted with multiple, patterned vacuum openings 15, as illustrated in FIG. 2 and a motor (not illustrated) is provided inside the base 16 for applying a vacuum to the vacuum openings 15 in the base plate 14 upon manipulation of a motor switch 19, also provided in the base 16. A heater switch 17 is also mounted in the base 16, along with a heater pilot light 18 for activating heating elements (not illustrated) located in the heating unit 8 and indicating when the heating elements are hot, respectively. The frame elevation knobs 13a are provided on the frame boss 11 for raising and lowering the frame boss 11 and the post seat 10a with respect to the base plate 14 and the heating unit 8, as hereinafter further described.

Figure 4:
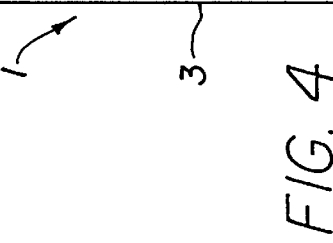
FIG. 4 is a top view of the gasket illustrated in FIG. 1.
Figure 5:
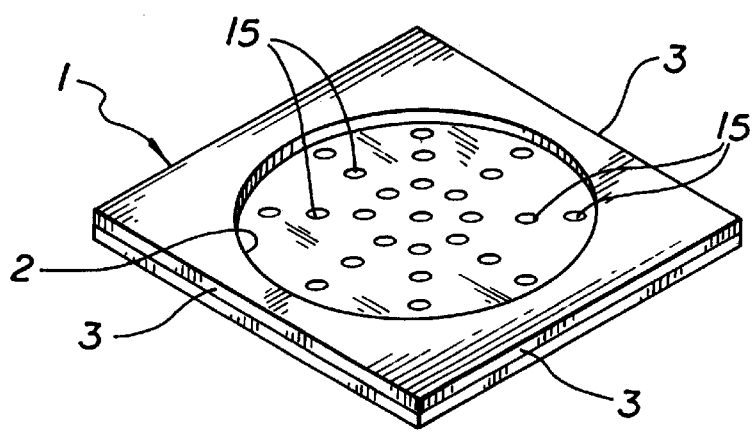
FIG. 5 is a perspective view of the gasket illustrated in FIGS. 1 and 4, positioned on the base plate illustrated in FIG. 2.
Figure 6:
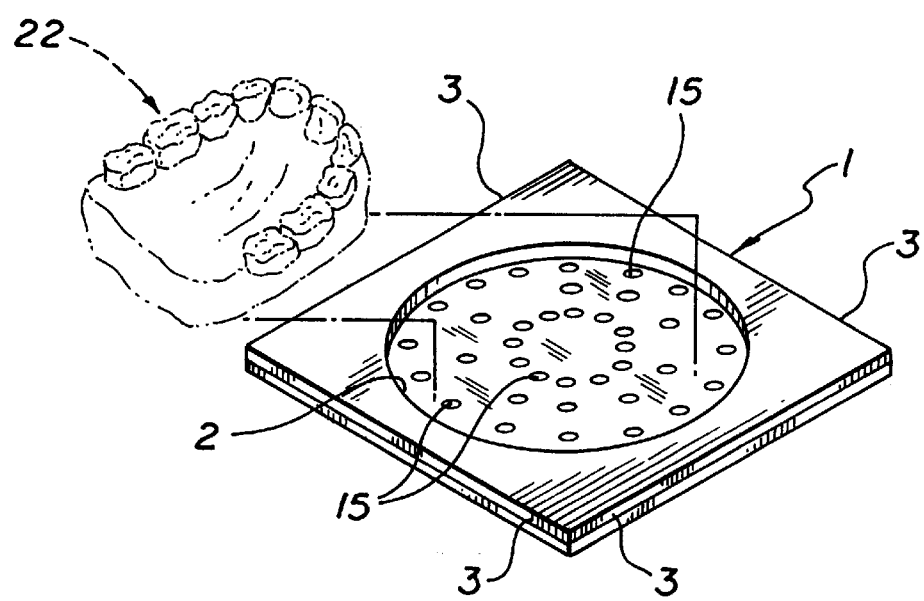
FIG. 6 is a perspective view of the gasket and base plate illustrated in FIGS. 1 and 4, positioned on the base plate illustrated in FIG. 3, with a dental impression cast, also positioned on the base plate.

Referring again to FIG. 1 and to FIGS. 4–6 of the drawings, a square gasket 1 is provided and is shaped to define gasket edges 3 of equal size. The gasket 1 has a flat top surface and a flat bottom surface and includes a round vacuum opening 2 in the center thereof, as illustrated. It will be appreciated that the gasket 1 is designed to fit inside the frame boss 11 of the vacuum thermoforming machine 7 with the gasket edges 3 adjacent to the boss edges 11a of the split frame boss 11, to block selected ones of the peripheral vacuum openings 15 in the base plate 14 and expose other of the center-oriented vacuum openings 15 which are aligned with the gasket vacuum opening 2 and the gasket 1, as illustrated in FIG. 5.

Figure 3:
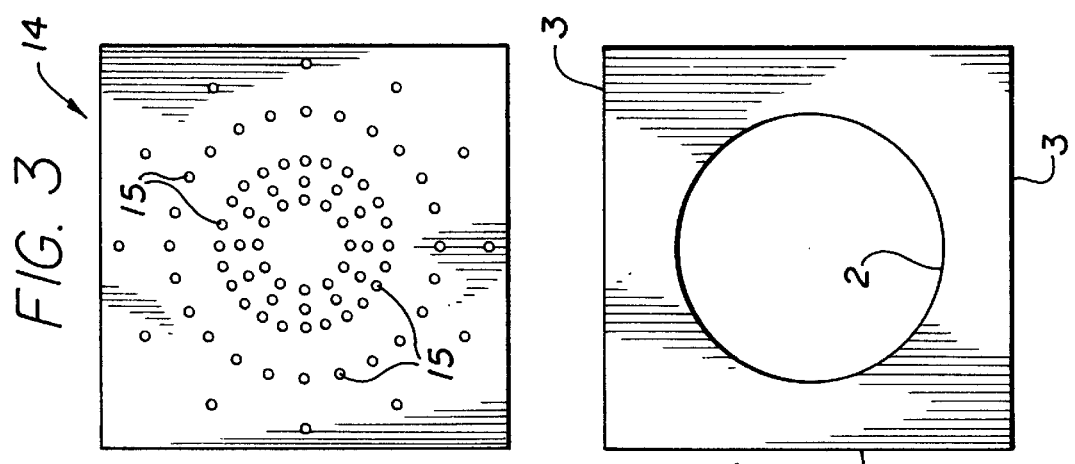
FIG. 3 is a top view of the perforated base plate illustrated in FIG. 2, modified to optimize the vacuum in the gasket opening when the gasket illustrated in FIG. 1 is seated on the base plate.

In a most preferred embodiment of the invention the vacuum openings 15 in the base plate 14 should be enlarged to about ⅛ of an inch in diameter and the number of vacuum openings 15 in the area of the gasket vacuum opening 2 is increased, as illustrated in FIGS. 3 and 6, although either of these expedients can be implemented independently of each other, to increase the vacuum in the exposed vacuum openings 15 in the gasket vacuum opening 2.

Figure 7:
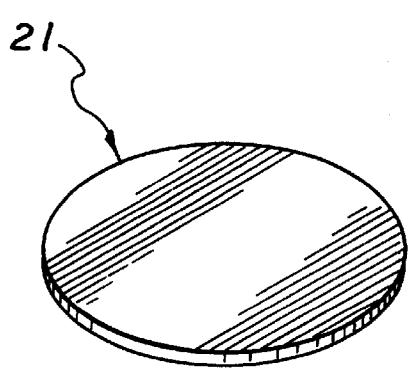
FIG. 7 is a perspective view of a plastic plate for encapsulating the teeth on the dental impression cast.

Accordingly, in operation, the gasket 1 of this invention is initially inserted in the square opening defined by the boss edges 11a of the frame boss 11 in the vacuum thermoforming machine 7. A dental impression cast 22, illustrated in phantom in FIG. 6, is then positioned on the base plate 14 inside the vacuum opening 2 and is exposed to those of the vacuum openings 15 which lie within the perimeter of the gasket vacuum opening 2. The frame elevation knobs 13a on the split frame boss 11 are then manipulated to raise the split frame boss 11 and the post seat 10a on the post 10 to a position intermediate the heating unit 8 and the base plate 14. The frame lock knob 13 is then manipulated to open the split frame boss 11 on the frame boss hinges 12 and insert a plastic plate 21, illustrated in FIG. 7, therebetween, after which the plastic plate 21 is securely locked in place by closing the split frame boss 11 and securing the frame lock knob 13. The heating unit 8 is then activated by manipulating the heater switch 17, whereupon the heater pilot light 18 in the base 16 is illuminated to indicate that the heating unit 8 is functioning properly. After two to three minutes, heat from the heating unit 8 softens the plastic plate 21 secured in the split frame boss 11, to the point where the softened plastic plate 21 can be molded over the dental impression cast 22 resting on the base plate 14, as illustrated in FIG. 6. The motor switch 19 is then activated to initiate a vacuum at the vacuum openings 15 which are exposed by the gasket vacuum opening 2 in the gasket 1 and the frame elevation knobs 13a are grasped and manipulated to facilitate sliding of the split frame boss 11 and the post seat 10a on the post 10. The split frame boss 11 is then forced rapidly downwardly to force the heat-softened plastic plate 21 over the dental impression cast 22 and allow the vacuum generated at the vacuum openings 15 exposed in the gasket vacuum opening 2 to pull the soft plastic plate 21 tightly around the teeth on the dental impression cast 22. The motor switch 19 and heater switch 17 are then manipulated to deactivate the heating and vacuum-producing elements of the vacuum thermoforming machine 7 and the dental impression cast 22, with the plastic overlay in place, is removed from the base plate 14. The plastic overlay is then allowed to cool and harden and is then cut from the dental impression cast 22 in order to shape a dental retainer or appliance of proper proportions, as required.

It will be appreciated by those skilled in the art that the gasket 1 of this invention can be shaped from substantially any heat-resistant, flexible material having a sealing quality, such as rubber. In a preferred embodiment the gasket 1 is formed of silicone rubber such as the commercial grade silicone "COMSIL", a trademark of West American Rubber Company. Furthermore, the gasket 1 and the procedure for using the gasket 1 can be utilized in substantially any vacuum thermoforming machine currently on the market and used by dental practitioners everywhere, with or without modification of the size and number of vacuum openings 15, as described herein and illustrated in FIGS. 3 and 6. Furthermore, the gasket 1 can be utilized in combination with plastic plates 21 of substantially any design, shape, thickness and character, it being only necessary that the plastic plate 21 be susceptible of being softened by the heating unit 8 in the vacuum thermoforming machine 7 to facilitate a tight fit over the dental impression cast 22 by operation of the improved and enhanced vacuum feature of the vacuum thermoforming machine 7, as heretofore described. However, in a most preferred embodiment of the invention the plastic sheet used in combination with the gasket 1 in conventional thermoforming machines to create the desired retainers and appliances is the "ESSIX" (trademark) plastic sheet, typically constructed of plastic material having a thickness of about 0.030 to about 0.040 of an inch. This material is crystal clear, abrasive resistant, FDA approved and has an excellent flex memory, wherein a superior snap-in fit of the vacuum-molded retainer or appliance is assured. After thermoforming, the thickness of the material is typically about 0.5 mm and it is light-reflective and esthetically pleasing, since it causes the teeth to shine brilliantly. The molded plastic is also sufficiently soft and can be easily shaped and treated to define an appliance or retainer which has good "memory" and is highly effective to straighten teeth.

While the preferred embodiments of this invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A gasket and a vacuum thermoforming machine for increasing the vacuum capacity of the vacuum thermoforming machine, said vacuum thermoforming machine having a base plate and vacuum openings provided in the base plate, and said gasket comprising a flexible, square, flat panel for positioning on the base plate over a first selected number of the vacuum openings and a round panel opening provided substantially in the center of said panel for exposing a second selected number of the vacuum openings, whereby the vacuum capacity of the vacuum thermoforming machine is increased in said second selected number of the vacuum openings.

2. The gasket of claim 1 wherein said panel is constructed of rubber.

3. A method of molding a plastic retainer for straightening teeth using a vacuum thermoforming maching having a base plate provided with multiple vacuum openings, said method comprising the steps of placing a gasket having a gasket opening over the base plate, with said gasket covering a selected first set of said vacuum openings and said gasket opening exposing a selected second set of said vacuum openings; positioning a plastic plate in the vacuum thermoforming machine above said gasket; placing a dental impression cast on the base plate in said gasket opening; heating the plastic plate in the vacuum thermoforming machine for softening the plastic plate; initiating a vacuum in the vacuum thermoforming machine at said selected second set of said vacuum openings in said gasket opening; and lowering the softened plastic plate over the dental impression cast to vacuum-form the softened plastic plate on the dental impression cast.

4. The method according to claim 3 comprising the step of increasing the number of said second set of said vacuum openings in the base plate in said gasket opening.

5. The method according to claim 3 comprising the step of increasing the size of said second set of said vacuum openings in the base plate in said gasket opening.

6. The method according to claim 3 comprising the steps of:

(a) increasing the number of said second set of said vacuum openings in the base plate in said gasket opening; and (b) increasing the size of said second set of said vacuum openings in the base plate in said gasket opening.

* * * * *